(12) United States Patent
Jiang

(10) Patent No.: US 12,631,636 B2
(45) Date of Patent: May 19, 2026

(54) PEPTIDOGLYCAN (PGN) APTAMERS AND ASSOCIATED METHODS

(71) Applicant: Fresenius Medical Care Holdings, Inc., Waltham, MA (US)

(72) Inventor: Tao Jiang, Knoxville, TN (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 1144 days.

(21) Appl. No.: 17/591,533

(22) Filed: Feb. 2, 2022

(65) Prior Publication Data

US 2022/0244255 A1        Aug. 4, 2022

Related U.S. Application Data

(60) Provisional application No. 63/145,635, filed on Feb. 4, 2021.

(51) Int. Cl.
*G01N 33/569* (2006.01)
*C12N 15/115* (2010.01)

(52) U.S. Cl.
CPC ...... *G01N 33/56911* (2013.01); *C12N 15/115* (2013.01); *C12N 2310/16* (2013.01); *C12N 2310/531* (2013.01)

(58) Field of Classification Search
CPC .............. C12N 15/115; C12N 2310/16; C12N 2310/531; G01N 33/56911; G01N 2333/4722
See application file for complete search history.

(56) References Cited

U.S. PATENT DOCUMENTS

| | | | |
|---|---|---|---|
| 9,958,448 B2 * | 5/2018 | Halbert ................ | C12N 15/115 |
| 2012/0210458 A9 * | 8/2012 | Cao .................... | C12N 15/8247 |
| | | | 435/320.1 |
| 2020/0249228 A1 | 8/2020 | Jiang et al. | |

OTHER PUBLICATIONS

Yang et al (DeepAptamer: Advancing high-affinity aptamer discovery with a hybrid deep learning model. Mol Ther Nucleic Acids. Dec. 21, 2024;36(1):102436. doi: 10.1016/j.omtn.2024.102436) (Year: 2024).*
Musumeci et al (Fluorescence Sensing Using DNA Aptamers in Cancer Research and Clinical Diagnostics. Cancers (Basel). Dec. 20, 2017;9(12):174. doi: 10.3390/cancers9120174) (Year: 201).*
Tsang, J. (Identifying Bacteria Through Look, Growth, Stain and Strain, American Society for Microbiology; obtained from: https:// asm.org/articles/2020/february/identifying-bacteria-through-look,-growth,-stain#:~:text=Early%20Microbial%20Identification%20Studies%20By,(acid%2Dfast%20staining) (Year: 2017).*
Ferreira et al. "Detection of bacterial infection by a technetium-99m-labeledpeptidoglycan aptamer" Biomedicine & Pharmacotherapy, vol. 93, Jul. 2017, pp. 931-938.
Ferreira et al. "Peptidoglycan aptamers biodistribution in infection bearing mice" Nuclear Medicine and Biomedical Imaging, vol. 3 , No. 2 , May 2018, pp. 1-4.
Graziani et al. "High Efficiency Binding Aptamers for a Wide Range of Bacterial Sepsis Agents" J. Microbiol. Biotechnol. vol. 27 , No. 4 , Jan. 24, 2017 (Jan. 24, 2017) , pp. 838-843.
Hong et al. "Single-Stranded DNA Aptamers against Pathogens and Toxins: Identification and Biosensing Applications" BioMed Research International vol. 2015 (Jun. 2015) 31 pages.
International Search Report for International Application No. PCT/US2022/014981, mailed Jul. 12, 2022, 10 pages.
International Written Opinion for International Application No. PCT/US2022/014981, mailed Jul. 12, 2022, 13 pages.
Ellington et al. "In vitro selection of RNA molecules that bind specific ligands" Nature (Aug. 1990) 346(6287) pp. 818-822.
Ferreira et al. "Selection of peptidoglycan-specific aptamers for bacterial cells identification." Appl Biochem Biotechnol. Dec. 2014; 174(7):2548-56. doi: 10.1007/s12010-014-1206-6. Epub Sep. 4, 2014. PMID: 25185503.
Gold et al. "Aptamers and the RNA world, past and present." Cold Spring Harb. Perspect. Biol. (Mar. 2012) 4(3), a003582.
Schütze et al. "Probing the SELEX Process with Next-Generation Sequencing" PLoS One 6(12): e29604 (Dec. 2011). DOI: 10.1371/journal.pone.0029604.
Tuerk et al. "Systematic evolution of ligands by exponential enrichment: RNA ligands to bacteriophage t4 DNA polymerase." Science (Aug. 1990) vol. 249, Issue 4968, pp. 505-510.
Wang et al. "Particle Display: A Quantitative Screening Method for Generating High-Affinity Aptamers" Angewandte Communications International Edition 53(19): pp. 4796-4801 (May 2014). DOI: 10.1002/anie.201309334.
Zhang "Synthesis of peptidoglycan peptides for DNA aptamer selection" (T). University of British Columbia (Oct. 2018). Retrieved from open.library.ubc.ca/collections/ubctheses/24/items/1.0372791.
Zhuo et al. "Recent Advances in SELEX Technology and Aptamer Applications in Biomedicine" Int. J. Mol. Sci. (Oct. 2017) 18(10), 2142; doi:10.3390/ijms18102142.
Zuker "Mfold web server for nucleic acid folding and hybridization prediction." Nucleic Acids Res. Vol. 31, Issue 13, pp. 3406-3415 (Jul. 2003).

* cited by examiner

*Primary Examiner* — Gregory S Emch
*Assistant Examiner* — Ashley H. Gao
(74) *Attorney, Agent, or Firm* — TraskBritt

(57)                    ABSTRACT

Described are a number of aptamers that are specific to bind with peptidoglycan ("PGN") with specificity over counter-targets lipopolysaccharides ("LPS") and lipoteichoic acid ("LTA"), and associated methods.

22 Claims, 10 Drawing Sheets

Specification includes a Sequence Listing.

SEQ ID NO:1

*FIG. 1*

SEQ ID NO:2

*FIG. 2*

SEQ ID NO:3

SEQ ID NO:4

*FIG. 4*

SEQ ID NO:5

*FIG. 5*

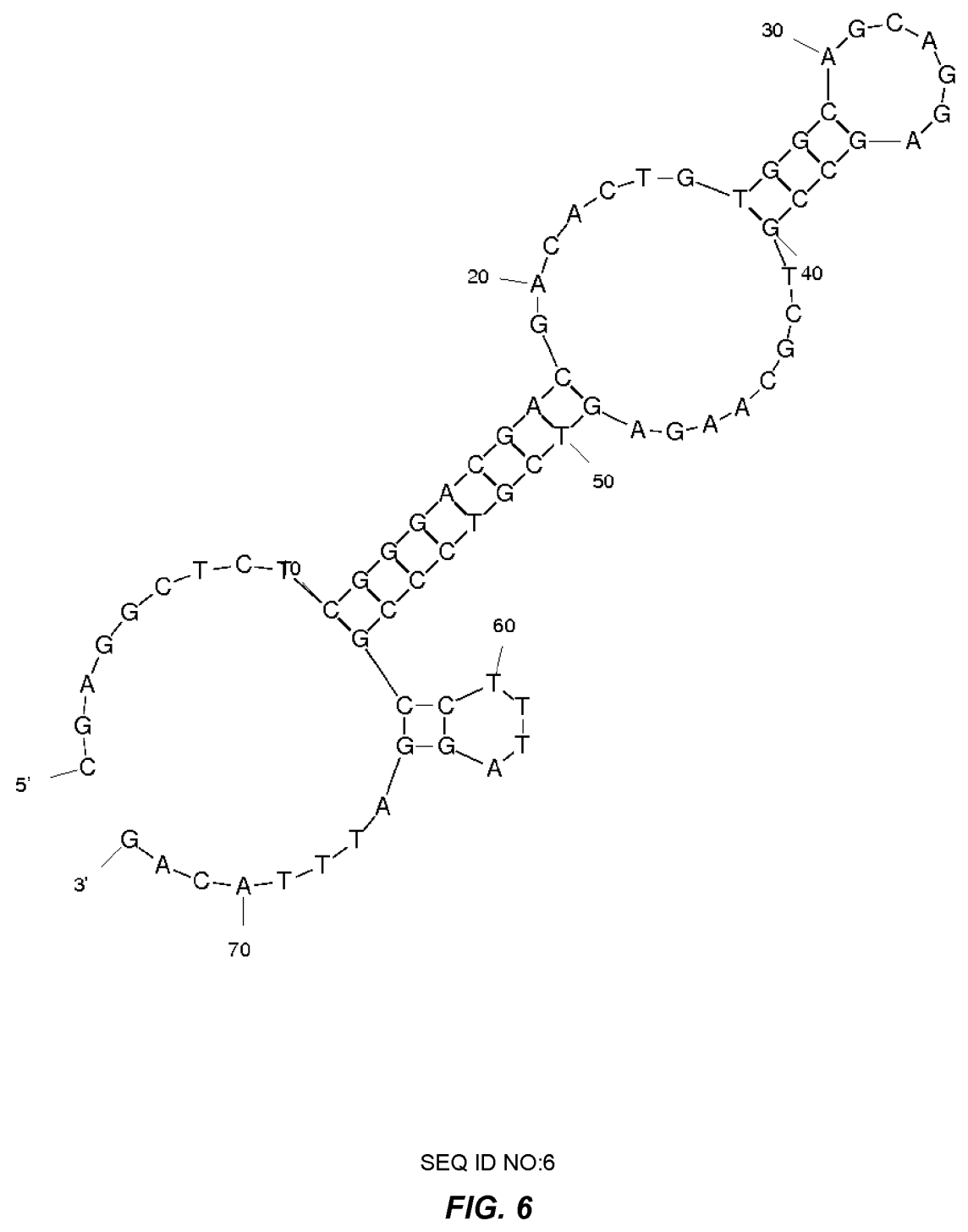

SEQ ID NO:6

*FIG. 6*

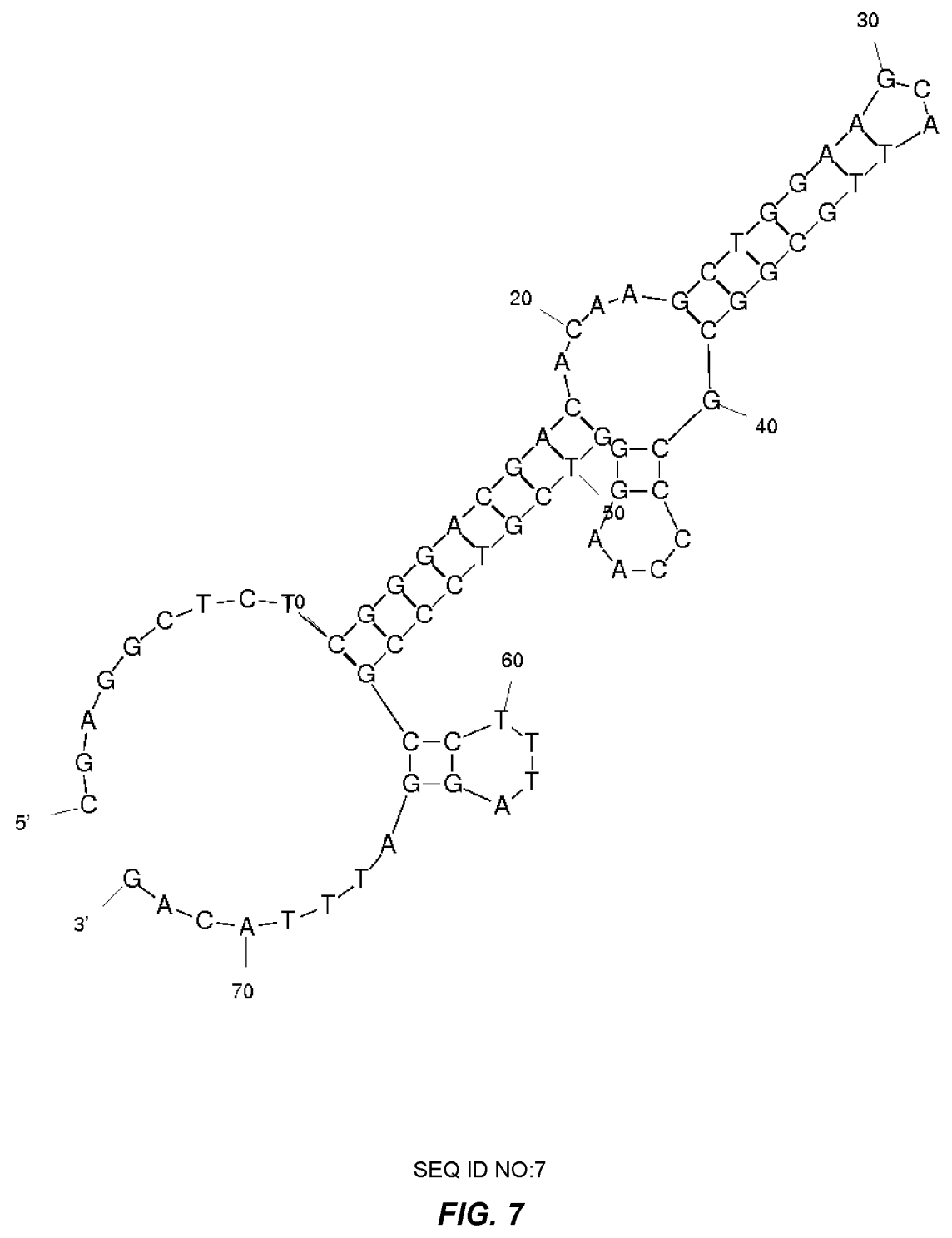

SEQ ID NO:7

*FIG. 7*

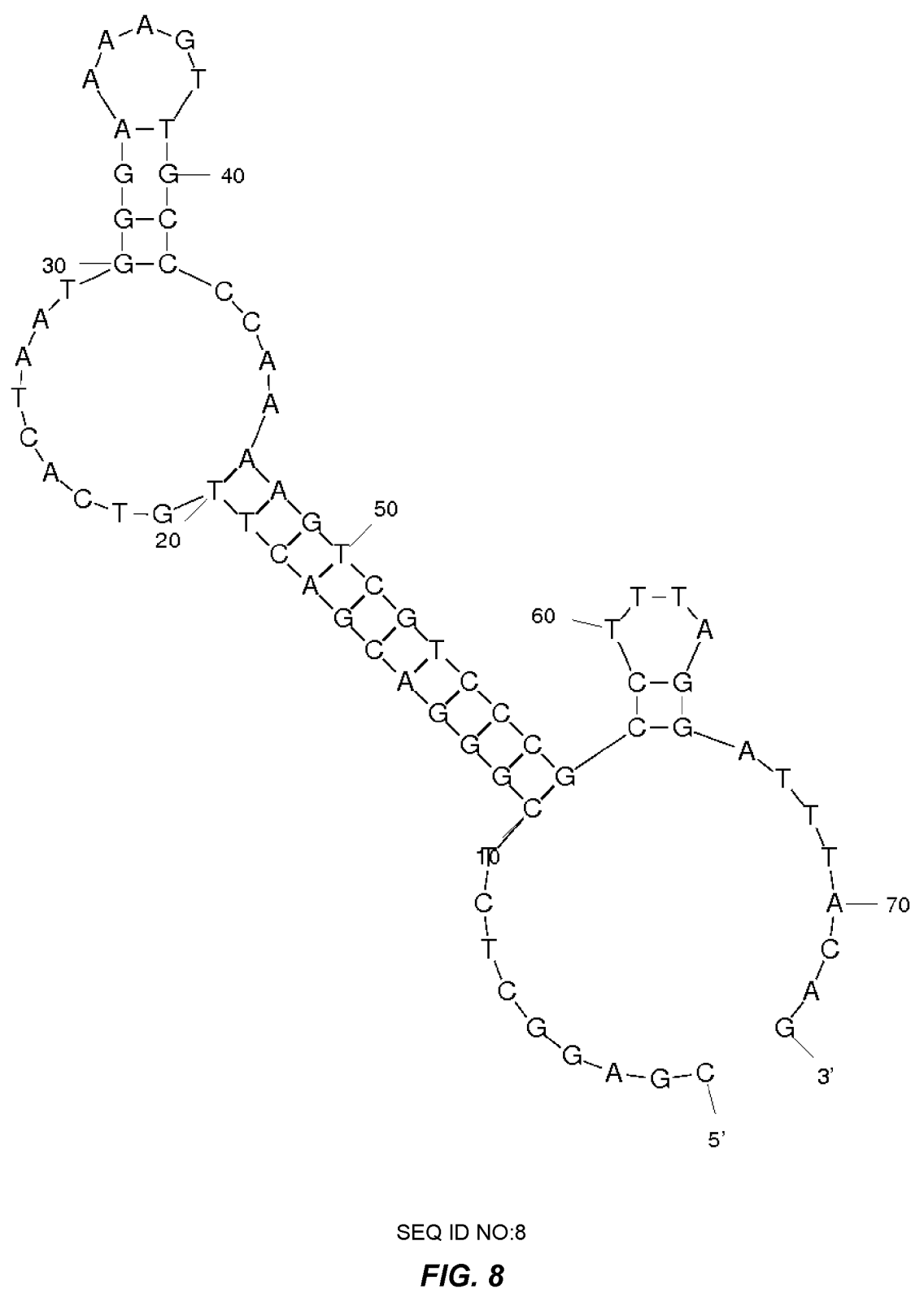

SEQ ID NO:8

*FIG. 8*

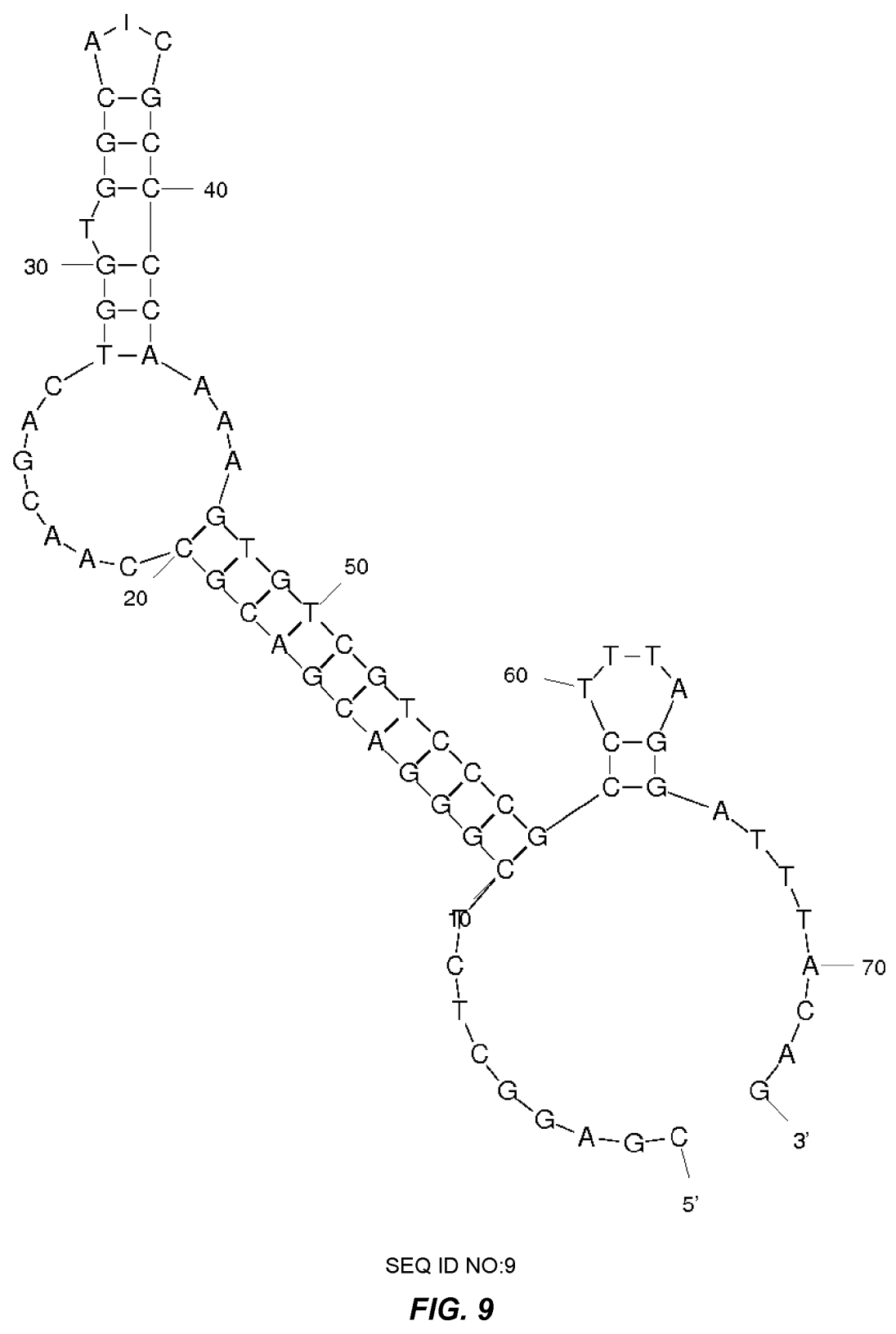

SEQ ID NO:9

*FIG. 9*

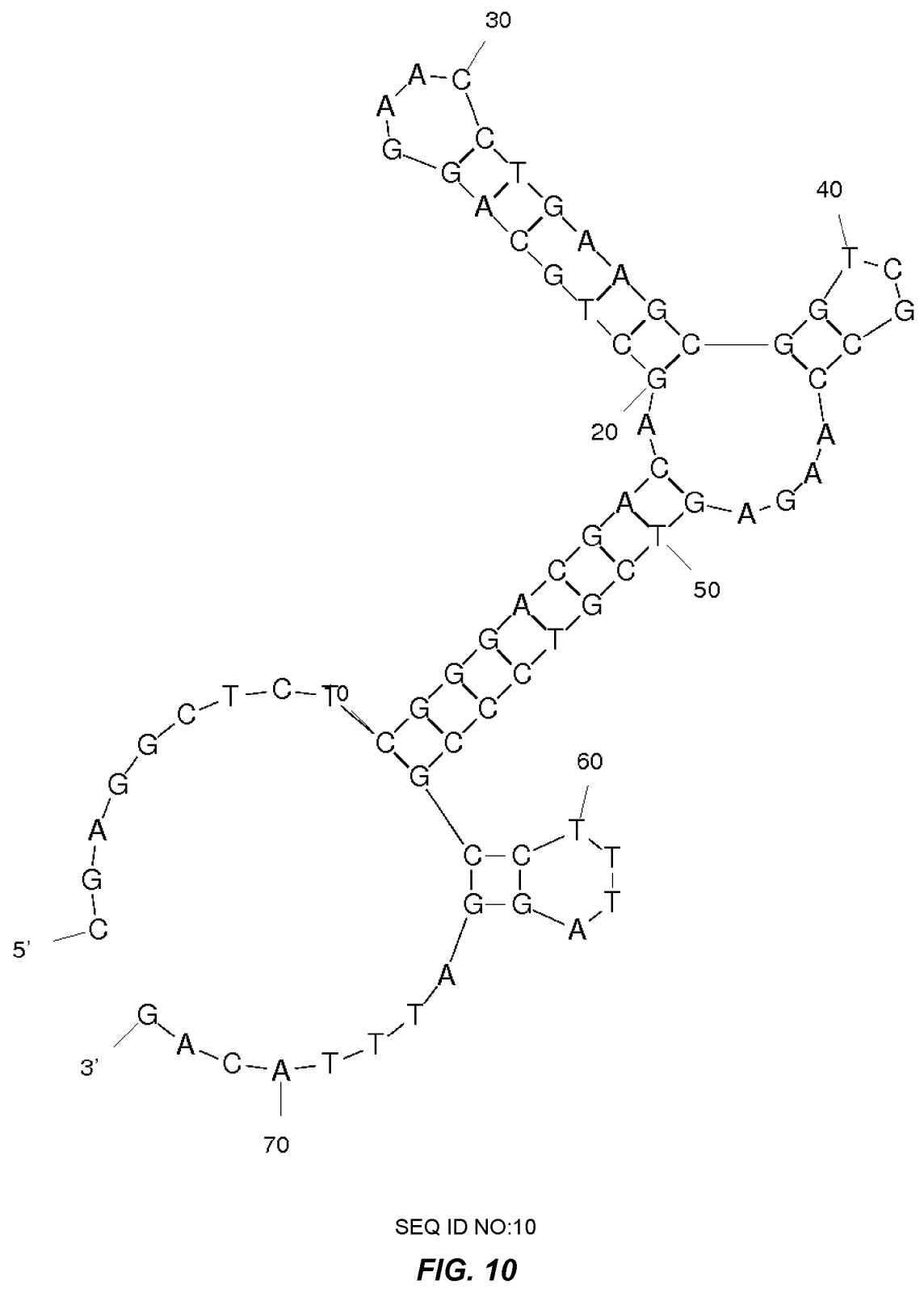

SEQ ID NO:10

*FIG. 10*

SEQUENCE LISTING

<160> NUMBER OF SEQ ID NOS: 24

<210> SEQ ID NO 1
<211> LENGTH: 73
<212> TYPE: DNA
<213> ORGANISM: Artificial Sequence

```
<220> FEATURE:
<223> OTHER INFORMATION: Exemplary DNA Aptamer

<400> SEQUENCE: 1
cgaggctctc gggacgacgt agtcgtcaca caaggcttaa ctcctaaagt cgtcccgcct      60
ttaggattta cag                                                        73

<210> SEQ ID NO 2
<211> LENGTH: 73
<212> TYPE: DNA
<213> ORGANISM: Artificial Sequence
<220> FEATURE:
<223> OTHER INFORMATION: Exemplary DNA Aptamer

<400> SEQUENCE: 2
cgaggctctc gggacgactg ggtacgtatg gacacagccg ttccaaaagt cgtcccgcct      60
ttaggattta cag                                                        73

<210> SEQ ID NO 3
<211> LENGTH: 73
<212> TYPE: DNA
<213> ORGANISM: Artificial Sequence
<220> FEATURE:
<223> OTHER INFORMATION: Exemplary DNA Aptamer

<400> SEQUENCE: 3
cgaggctctc gggacgacaa agggctagtg ccatttatcg gcccaaaagt cgtcccgcct      60
ttaggattta cag                                                        73

<210> SEQ ID NO 4
<211> LENGTH: 73
<212> TYPE: DNA
<213> ORGANISM: Artificial Sequence
<220> FEATURE:
<223> OTHER INFORMATION: Exemplary DNA Aptamer

<400> SEQUENCE: 4
cgaggctctc gggacgacga gcgcattaaa gcgcaagccg ggccgtaagt cgtcccgcct      60
ttaggattta cag                                                        73

<210> SEQ ID NO 5
<211> LENGTH: 73
<212> TYPE: DNA
<213> ORGANISM: Artificial Sequence
<220> FEATURE:
<223> OTHER INFORMATION: Exemplary DNA Aptamer

<400> SEQUENCE: 5
cgaggctctc gggacgacta caccggaacg acttgccgcg caggtatagt cgtcccgcct      60
ttaggattta cag                                                        73

<210> SEQ ID NO 6
<211> LENGTH: 73
<212> TYPE: DNA
<213> ORGANISM: Artificial Sequence
<220> FEATURE:
<223> OTHER INFORMATION: Exemplary DNA Aptamer

<400> SEQUENCE: 6
cgaggctctc gggacgacga cactgtggca gcaggagccg tcgcaagagt cgtcccgcct      60
ttaggattta cag                                                        73
```

-continued

```
<210> SEQ ID NO 7
<211> LENGTH: 73
<212> TYPE: DNA
<213> ORGANISM: Artificial Sequence
<220> FEATURE:
<223> OTHER INFORMATION: Exemplary DNA Aptamer

<400> SEQUENCE: 7
cgaggctctc gggacgacac aagctggaag cattgcggcg ccccaagggt cgtcccgcct      60
ttaggattta cag                                                        73

<210> SEQ ID NO 8
<211> LENGTH: 73
<212> TYPE: DNA
<213> ORGANISM: Artificial Sequence
<220> FEATURE:
<223> OTHER INFORMATION: Exemplary DNA Aptamer

<400> SEQUENCE: 8
cgaggctctc gggacgactt gtcactaatg ggaaaagttg ccccaaaagt cgtcccgcct      60
ttaggattta cag                                                        73

<210> SEQ ID NO 9
<211> LENGTH: 73
<212> TYPE: DNA
<213> ORGANISM: Artificial Sequence
<220> FEATURE:
<223> OTHER INFORMATION: Exemplary DNA Aptamer

<400> SEQUENCE: 9
cgaggctctc gggacgacgc caacgactgg tggcatcgcc ccaaaagtgt cgtcccgcct      60
ttaggattta cag                                                        73

<210> SEQ ID NO 10
<211> LENGTH: 73
<212> TYPE: DNA
<213> ORGANISM: Artificial Sequence
<220> FEATURE:
<223> OTHER INFORMATION: Exemplary DNA Aptamer

<400> SEQUENCE: 10
cgaggctctc gggacgacag ctgcaggaac ctgaagcggt cgccaagagt cgtcccgcct      60
ttaggattta cag                                                        73

<210> SEQ ID NO 11
<211> LENGTH: 30
<212> TYPE: DNA
<213> ORGANISM: Artificial Sequence
<220> FEATURE:
<223> OTHER INFORMATION: Core Sequence

<400> SEQUENCE: 11
gtagtcgtca cacaaggctt aactcctaaa                                      30

<210> SEQ ID NO 12
<211> LENGTH: 30
<212> TYPE: DNA
<213> ORGANISM: Artificial Sequence
<220> FEATURE:
<223> OTHER INFORMATION: Core Sequence

<400> SEQUENCE: 12
tgggtacgta tggacacagc cgttccaaaa                                      30
```

-continued

```
<210> SEQ ID NO 13
<211> LENGTH: 30
<212> TYPE: DNA
<213> ORGANISM: Artificial Sequence
<220> FEATURE:
<223> OTHER INFORMATION: Core Sequence

<400> SEQUENCE: 13
aaagggctag tgccatttat cggcccaaaa                                      30

<210> SEQ ID NO 14
<211> LENGTH: 30
<212> TYPE: DNA
<213> ORGANISM: Artificial Sequence
<220> FEATURE:
<223> OTHER INFORMATION: Core Sequence

<400> SEQUENCE: 14
gagcgcatta aagcgcaagc cgggccgtaa                                      30

<210> SEQ ID NO 15
<211> LENGTH: 30
<212> TYPE: DNA
<213> ORGANISM: Artificial Sequence
<220> FEATURE:
<223> OTHER INFORMATION: Core Sequence

<400> SEQUENCE: 15
tacaccggaa cgacttgccg cgcaggtata                                      30

<210> SEQ ID NO 16
<211> LENGTH: 27
<212> TYPE: DNA
<213> ORGANISM: Artificial Sequence
<220> FEATURE:
<223> OTHER INFORMATION: Core Sequence

<400> SEQUENCE: 16
actgtggcag caggagccgt cgcaaga                                         27

<210> SEQ ID NO 17
<211> LENGTH: 30
<212> TYPE: DNA
<213> ORGANISM: Artificial Sequence
<220> FEATURE:
<223> OTHER INFORMATION: Core Sequence

<400> SEQUENCE: 17
acaagctgga agcattgcgg cgccccaagg                                      30

<210> SEQ ID NO 18
<211> LENGTH: 30
<212> TYPE: DNA
<213> ORGANISM: Artificial Sequence
<220> FEATURE:
<223> OTHER INFORMATION: Core Sequence

<400> SEQUENCE: 18
ttgtcactaa tgggaaaagt tgccccaaaa                                      30

<210> SEQ ID NO 19
<211> LENGTH: 30
<212> TYPE: DNA
<213> ORGANISM: Artificial Sequence
<220> FEATURE:
```

-continued

```
<223> OTHER INFORMATION: Core Sequence

<400> SEQUENCE: 19
gccaacgact ggtggcatcg ccccaaaagt                                    30

<210> SEQ ID NO 20
<211> LENGTH: 30
<212> TYPE: DNA
<213> ORGANISM: Artificial Sequence
<220> FEATURE:
<223> OTHER INFORMATION: Core Sequence

<400> SEQUENCE: 20
agctgcagga acctgaagcg gtcgccaaga                                    30

<210> SEQ ID NO 21
<211> LENGTH: 21
<212> TYPE: DNA
<213> ORGANISM: Artificial Sequence
<220> FEATURE:
<223> OTHER INFORMATION: DNA Aptamer
<220> FEATURE:
<221> NAME/KEY: h
<222> LOCATION: (2)..(2)
<223> OTHER INFORMATION: A, C, or T
<220> FEATURE:
<221> NAME/KEY: v
<222> LOCATION: (4)..(4)
<223> OTHER INFORMATION: A, C, or G
<220> FEATURE:
<221> NAME/KEY: n
<222> LOCATION: (5)..(10)
<223> OTHER INFORMATION: A, C, G, or T
<220> FEATURE:
<221> NAME/KEY: misc_feature
<222> LOCATION: (5)..(10)
<223> OTHER INFORMATION: n is a, c, g, or t
<220> FEATURE:
<221> NAME/KEY: b
<222> LOCATION: (11)..(11)
<223> OTHER INFORMATION: C, G, or T
<220> FEATURE:
<221> NAME/KEY: b
<222> LOCATION: (14)..(14)
<223> OTHER INFORMATION: C, G, or T
<220> FEATURE:
<221> NAME/KEY: n
<222> LOCATION: (15)..(15)
<223> OTHER INFORMATION: A, C, G, or T
<220> FEATURE:
<221> NAME/KEY: d
<222> LOCATION: (15)..(15)
<223> OTHER INFORMATION: A, G, or T
<220> FEATURE:
<221> NAME/KEY: misc_feature
<222> LOCATION: (15)..(15)
<223> OTHER INFORMATION: n is a, c, g, or t

<400> SEQUENCE: 21
ahgvnnnnnn bcgbnccaad a                                             21

<210> SEQ ID NO 22
<211> LENGTH: 18
<212> TYPE: DNA
<213> ORGANISM: Artificial Sequence
<220> FEATURE:
<223> OTHER INFORMATION: Primer Sequence

<400> SEQUENCE: 22
cgaggctctc gggacgac                                                18
```

-continued

```
<210> SEQ ID NO 23
<211> LENGTH: 25
<212> TYPE: DNA
<213> ORGANISM: Artificial Sequence
<220> FEATURE:
<223> OTHER INFORMATION: Primer Sequence

<400> SEQUENCE: 23
gtcgtcccgc ctttaggatt tacag                                          25

<210> SEQ ID NO 24
<211> LENGTH: 19
<212> TYPE: DNA
<213> ORGANISM: Artificial Sequence
<220> FEATURE:
<223> OTHER INFORMATION: Reporter
<220> FEATURE:
<221> NAME/KEY: n
<222> LOCATION: (19)..(19)
<223> OTHER INFORMATION: 3Cy5Sp
<220> FEATURE:
<221> NAME/KEY: misc_feature
<222> LOCATION: (19)..(19)
<223> OTHER INFORMATION: n is a, c, g, or t

<400> SEQUENCE: 24
gtcgtcccga gagcctcgn                                                 19
```

PEPTIDOGLYCAN (PGN) APTAMERS AND ASSOCIATED METHODS

CROSS-REFERENCE TO RELATED APPLICATION

This application claims the benefit under 35 U.S.C. § 119(e) of U.S. Provisional Patent Application Ser. No. 63/145,635, filed Feb. 4, 2021, the disclosure of which is hereby incorporated herein in its entirety by this reference.

TECHNICAL FIELD

This application relates generally to biochemistry, and more particularly to aptamers that specifically bind to peptidoglycan (PGN) and associated methods.

STATEMENT ACCORDING TO 37 C.F.R. § 1.821(c) or (e)-SEQUENCE LISTING SUBMITTED AS A TXT AND PDF FILES

Pursuant to 37 C.F.R. § 1.821(c) or (e), files containing a TXT version and a PDF version of the Sequence Listing have been submitted concomitant with this application, the contents of which are hereby incorporated by reference.

BACKGROUND

As described in Ferreira et al. "Selection of peptidoglycan-specific aptamers for bacterial cells identification." *Appl Biochem Biotechnol.* 2014 Dec; 174(7):2548-56, peptidoglycan ("PGN") "is a highly complex and essential macromolecule of bacterial outer cell wall; it is a heteropolymer made up of linear glycan strands cross-linked by peptides. Peptidoglycan has a particular composition which makes it a possible target for specific bacterial recognition."

Aptamers are short strands of oligonucleotides that form a three-dimensional structure able to bind a target material with high affinity and specificity. Aptamers can, for example, be used as elements of biosensors that can recognize molecules in detection and analysis systems, similar to antibodies.

The purpose of the study in Ferreira et al. "was to obtain aptamers for use as radiopharmaceutical in bacterial infection diagnosis. Two aptamers against peptidoglycan were selected through the Systematic Evolution of Ligands by Exponential Enrichment (SELEX) methodology." The aptamers were labeled with $^{32}$P and showed high affinity for Staphylococcus aureus cells. "The binding to *S. aureus* and *Escherichia coli* in vitro were significantly higher than for *Candida albicans* and human fibroblasts, demonstrating their specificity for bacterial cells." Id. See, also, Zhang, W. "Synthesis of peptidoglycan peptides for DNA aptamer selection" (T). University of British Columbia (2018).

SUMMARY OF THE DISCLOSURE

Described herein are particularly useful DNA aptamers to PGN with specificity over counter-targets lipopolysaccharides ("LPS") and lipoteichoic acid ("LTA").

In certain embodiments, such an aptamer has a loop structure. In certain embodiments, such an aptamer has a double-stranded stem structure. In certain embodiments, such an aptamer further comprises at least one labeling substance such as an optical label, an electrochemical label, a radioisotope, or a combination thereof.

Specifically described are the exemplary DNA aptamers of SEQ ID NOs: 1-10.

```
(5'->3') (SEQ ID NO: 1):
CGA GGC TCT CGG GAC GAC GTA GTC GTC

ACA CAA GGC TTA ACT CCT AAA GTC GTC

CCG CCT TTA GGA TTT ACA G;

(5'->3') (SEQ ID NO: 2):
CGA GGC TCT CGG GAC GAC TGG GTA CGT

ATG GAC ACA GCC GTT CCA AAA GTC GTC

CCG CCT TTA GGA TTT ACA G;

(5'->3') (SEQ ID NO: 3):
CGA GGC TCT CGG GAC GAC AAA GGG CTA

GTG CCA TTT ATC GGC CCA AAA GTC GTC

CCG CCT TTA GGA TTT ACA G;

(5'->3') (SEQ ID NO: 4):
CGA GGC TCT CGG GAC GAC GAG CGC ATT

AAA GCG CAA GCC GGG CCG TAA GTC GTC

CCG CCT TTA GGA TTT ACA G;

(5'->3') (SEQ ID NO: 5):
CGA GGC TCT CGG GAC GAC TAC ACC GGA

ACG ACT TGC CGC GCA GGT ATA GTC GTC

CCG CCT TTA GGA TTT ACA G;

(5'->3') (SEQ ID NO: 6):
CGA GGC TCT CGG GAC GAC GAC ACT GTG

GCA GCA GGA GCC GTC GCA AGA GTC GTC

CCG CCT TTA GGA TTT ACA G;

(5'->3'):
(SEQ ID NO 7):
CGA GGC TCT CGG GAC GAC ACA AGC TGG

AAG CAT TGC GGC GCC CCA AGG GTC GTC

CCG CCT TTA GGA TTT ACA G;

(5'->3') (SEQ ID NO: 8):
CGA GGC TCT CGG GAC GAC TTG TCA CTA

ATG GGA AAA GTT GCC CCA AAA GTC GTC

CCG CCT TTA GGA TTT ACA G;

(5'->3') (SEQ ID NO: 9):
CGA GGC TCT CGG GAC GAC GCC AAC GAC

TGG TGG CAT CGC CCC AAA AGT GTC GTC

CCG CCT TTA GGA TTT ACA G;
and (5'->3') (SEQ ID NO: 10):
CGA GGC TCT CGG GAC GAC AGC TGC AGG

AAC CTG AAG CGG TCG CCA AGA GTC GTC

CCG CCT TTA GGA TTT ACA G.
```

3

As can be seen, the "core sequences" of these aptamers are, respectively, SEQ ID NOs: 11-20:

```
(SEQ ID NO: 11):
GTA GTC GTC ACA CAA GGC TTA ACT CCT AAA;

(SEQ ID NO: 12):
TGG GTA CGT ATG GAC ACA GCC GTT CCA AAA;

(SEQ ID NO: 13):
AAA GGG CTA GTG CCA TTT ATC GGC CCA AAA;

(SEQ ID NO: 14):
GAG CGC ATT AAA GCG CAA GCC GGG CCG TAA;

(SEQ ID NO: 15):
TAC ACC GGA ACG ACT TGC CGC GCA GGT ATA;

(SEQ ID NO: 16):
ACT GTG GCA GCA GGA GCC GTC GCA AGA;

(SEQ ID NO: 17):
ACA AGC TGG AAG CAT TGC GGC GCC CCA AGG;

(SEQ ID NO: 18):
TTG TCA CTA ATG GGA AAA GTT GCC CCA AAA;

(SEQ ID NO: 19):
GCC AAC GAC TGG TGG CAT CGC CCC AAA AGT;
and (SEQ ID NO: 20):
AGC TGC AGG AAC CTG AAG CGG TCG CCA AGA.
```

In certain embodiments, the DNA aptamer core sequence includes:

AHG VNN NNN NBC GBN CCA ADA (SEQ ID NO: 21)

wherein A, C, G, and T have their customary meanings, wherein V is A, C, or G; wherein B is C, G, or T; wherein D is A, G, or T; wherein H is A, C, or T; and wherein N is A, C, G, or T.

The aptamers of SEQ ID NOs: 1-10 also include PCR primer annealing regions (or "primer sequences") (5'-CGA GGC TCT CGG GAC GAC (SEQ ID NO:22)—[core sequence]—GTC GTC CCG CCT TTA GGA TTT ACA G-3' (SEQ ID NO:23)), although other PCR primer annealing regions may be used so long as they do not interfere with the binding of the aptamer to PGN.

Thus, described is a DNA aptamer comprising a polynucleotide of any of the following (a) to (c) and capable of binding to peptidoglycan ("PGN"): (a) a polynucleotide comprising a core sequence set forth in any one of SEQ ID NOs: 11-21, (b) a polynucleotide comprising a core sequence having the deletion, substitution, insertion and/or addition of one to two bases in the core sequence set forth in any one of SEQ ID NOs: 11-21, and (c) a polynucleotide comprising a core sequence having a sequence identity of 90% or more to the core sequence set forth in any one of SEQ ID NOs: 11-21.

In certain embodiments, provided is a method for detecting PGN, including binding an aptamer as described herein to PGN to thereby detect the PGN.

Thus, further described herein are the DNA aptamers and their use for detecting PGN.

Also described herein is a method for first detecting the presence of bacteria in a sample (e.g., a peritoneal dialysis effluent), and then further characterizing the detected bacteria afterword as Gram negative or Gram positive. In certain embodiments of such a method, first an anti-PGN aptamer (which may be labeled, e.g., with an appropriate quenching fluorescence pair) is first used to detect the presence of PGN in a sample. Since PGN is a cell wall component of all bacteria, its presence indicates bacteria being in the sample, no matter what the species. The sample is then further contacted (e.g., by microfluidic direction) with appropriately labeled anti-LPS and/or anti-LTA aptamers, which are used to detect the presence of LPS and/or LTA. The presence of LPS and LTA as determined by these later aptamers indicate that Gram negative and Gram positive bacteria, respectively, are contained within the sample. Thus further described is an assay comprising aptamers to PGN, LTA and/or LPS, which aptamers are configured in the assay for consecutive work flow (e.g., PGN first, and then LTA and/or LPS), useful to detect the presence of bacteria in a sample and characterize the detected bacteria as either Gram negative or Gram positive. This information can be used to appropriately select an antibiotic for treatment of a subject from whom the sample has been taken.

BRIEF DESCRIPTION OF THE DRAWINGS

FIGS. 1-5 show the predicted secondary structures of the DNA aptamers of SEQ ID NOs: 1-5, respectively.
FIGS. 6-10 show the predicted secondary structures of the DNA aptamers of SEQ ID NOs: 6-10, respectively.

DETAILED DESCRIPTION

Figure 3:
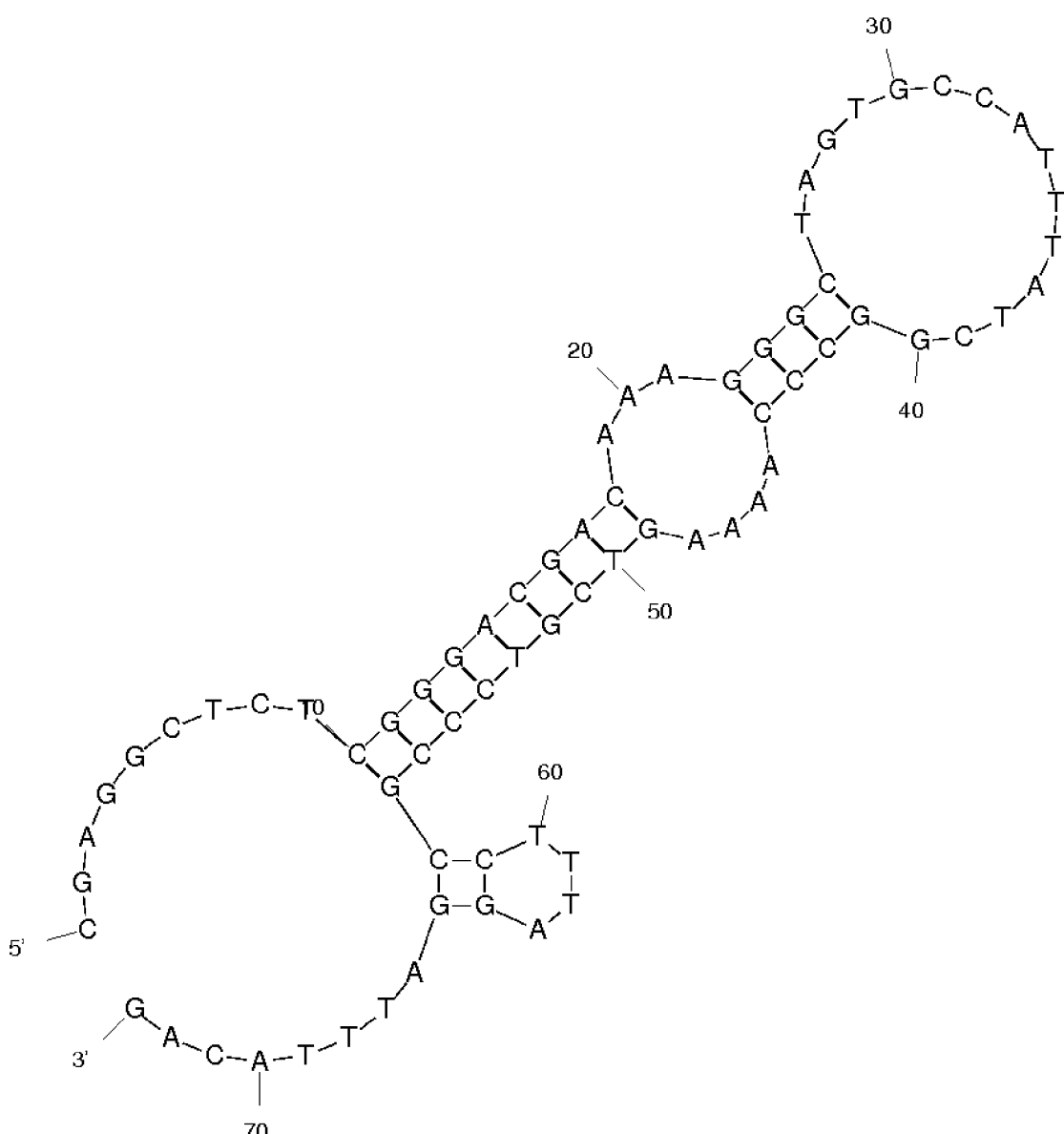

The term "base pairing", as used herein, refers to base pairing formed of a pair of complementary synthetic bases, such as adenine and thymine or guanine and cytosine.

The term "DNA aptamer", as used herein, refers to an aptamer sequence composed of DNA nucleotides. A DNA aptamer is a ligand molecule that firmly and specifically binds to a target molecule through a conformational structure formed based upon a secondary and a tertiary structure of a single-stranded nucleic acid molecule via hydrogen bonding or other interactions.

The term "target molecule," as used herein, refers to a substance to which the DNA aptamer can bind. As used herein, a target molecule is PGN.

In one aspect, described is an agent for detecting PGN, the agent comprising a DNA aptamer as described herein. In certain embodiments, the agent for detecting PGN is an agent that is used for detecting PGN in vitro utilizing the ability of a described DNA aptamer to bind to PGN. For example, the DNA aptamer is labeled with a fluorescence reagent beforehand, and the labeled DNA aptamer is admixed with a sample.

In one aspect, described is a composition for detecting PGN, the composition comprising a DNA aptamer as described herein.

In principle, the composition may be prepared in accordance with a method known in the art. For example, see the method described in Remington's Pharmaceutical Sciences (Merck Publishing Co., Easton, Pa.)

For example, preparations can be prepared by a method generally used in the art, comprising dissolving at least one DNA aptamer hereof in, for example, a pharmaceutically acceptable solvent and adding, for example, a pharmaceutically acceptable carrier thereto, if needed.

Examples of "pharmaceutically acceptable solvent(s)" include water, ethanol, propylene glycol, ethoxylated isostearyl alcohol, polyoxylated isostearyl alcohol, and a polyoxyethylene sorbitan fatty acid ester.

In one aspect, the disclosure relates to a kit for detecting PGN or for more generally detecting bacteria in a sample, the kit comprising a DNA aptamer as described herein. In addition to the DNA aptamer as described herein, the kit as described herein may comprise, for example, a buffer, a label reagent, and/or instructions.

In certain embodiments, the aptamer is labeled with a labeling substance, and detection of the PGN may occur by detecting the labeling substance. Examples of labeling substances include a dye, a fluorescent dye, a radioisotope, an antibody, an antigen, and an enzyme. Examples of the fluorescent dye include FITC. Such labels may be attached to a specific base or a specific structure of the aptamer, for example, a specific site of a hairpin-loop structure or a 3' or 5' terminus of an aptamer.

An optical label may be exemplified by a fluorescent material. For example, the fluorescent material may be selected from among fluorescein, 6-FAM, rhodamine, Texas Red, tetramethyl rhodamine, carboxyl rhodamine, carboxyl rhodamine 6G, carboxyl rhodol, carboxyl rhodamine 110, Cascade Blue, Cascade Yellow, coumarin, Cy2 (cyanine 2), Cy3, Cy3.5, Cy5, Cy5.5, Cy-chromium, phycoerythrin, PerCP (peridinin chlorophyll—a protein), PerCP-Cy5.5, JOE (6-carboxy-4',5'-dichloro-2',7'-dimethoxyfluorescin), NED, ROX (5-(and-6)-carboxy-X-rhodamine), HEX, Lucifer Yellow, Marina Blue, Oregon Green 488, Oregon Green 500, Oregon Green 514, Alexa Fluor, 7-amino-4-methylcoumarin-3-acetic acid, BODIPY FL, BODIPY FL-Br 2, BODIPY 530/550, conjugations thereof, and combinations thereof.

The optical label may be an enzyme, suitable for use in enzyme-linked immunosorbent assay ("ELISA"). The enzyme used for ELISA may include alkaline phosphatase, horseradish peroxidase, luciferase, or glucose oxidase. When the enzyme is used as the optical label, a chemiluminescent material may be employed in order to induce a chemiluminescent reaction, the chemiluminescent material being selected from among luminol, isoluminol, luciferin, lucigenin, 3-(2'-spiroadamantane)-4-methoxy-4-(3"-phosphoryloxy)phenyl-1,2-dioxetan-e (AMPPD), and disodium 3-(4-methoxyspiro {1,2-dioxetane-3,2'-(5'-chloro)tricyclo [3.3.1.13,7]decan}-4-yl)phenyl phosphate (CSPD). In addition thereto, any material appropriately selected by those skilled in the art is useful.

An optical label may be a fluorescence resonance energy transfer ("FRET") pair, which includes a donor fluorophore and an acceptor fluorophore spaced apart from each other by an appropriate distance and in which the fluorescence emission of the donor is suppressed or quenched by the acceptor. The donor fluorophore may include FAM, TAMRA, VIC, JOE, Cy3, Cy5 and Texas Red. The acceptor fluorophore may be selected so as to overlap its excitation spectrum with the emission spectrum of the donor. The acceptor may be a non-fluorescence acceptor for quenching a wide range of donor.

Also described herein is an aptamer-immobilized carrier in which the aptamer for detecting PGN (or a multi-structure aptamer thereof) is immobilized on the surface of a solid phase carrier. As the solid phase carrier, it is possible to employ carriers of various shapes such as sheet-like, plate-like, cylindrical, and spherical carriers. As the material for a carrier, a plastic, metal, glass, or the like may be used. Typically, any material may be used so long as it is a material able to have an aptamer immobilized thereto, for example for use with a lateral flow assay device. (See, e.g., U.S. Patent Application Publication 20200249228 A1 to Jiang et al. (Aug. 6, 2020) for "Rapid Diagnosis of Peritonitis in Peritoneal Dialysis Patients", the contents of which are incorporated herein by this reference.) For example, an aptamer-immobilized carrier may be a carrier in which the aptamer is immobilized on the surface of a sheet-like solid phase carrier.

The invention is further described with the aid of the following illustrative Examples.

Examples

Example I

After screening a nucleic acid library over several generations against the target peptidoglycan (PGN) for specificity over counter-targets lipoteichoic acid ("LTA") and lipopolysaccharides ("LPS"), the enriched library was processed to identify aptamer candidates. Libraries produced by initial screening were sequenced for used in the differential analysis and identification of the most promising aptamer sequences in terms of binding performance. These candidates were qualitatively assessed for response to PGN in 1× SELEX buffer before the best candidates were characterized.

As will be appreciated by those of skill in the art, SELEX begins with the synthesis of a very large oligonucleotide library consisting of randomly generated sequences of fixed length flanked by constant 5' and 3' ends that serve as primers. For a randomly generated region of length n, the number of possible sequences in the library is 4n (n positions with four possibilities (A, T, C, or G) at each position). The sequences in the library are exposed to the target ligand—which may be a protein or a small organic compound—and those that do not bind the target are removed, usually by affinity chromatography or target capture on paramagnetic beads. The bound sequences are eluted and amplified by PCR to prepare for subsequent rounds of selection in which the stringency of the elution conditions can be increased to identify the tightest-binding sequences.

Sequencing: The initial library was subjected to eight rounds of Melting-Off selection followed by parallel assessment. The SELEX process enriches for sequences over multiple rounds of selection that bind to PGN, and remove sequences that respond to components of 1× SELEX buffer or LTA. As a result, the population to be sequenced should contain multiple copies of potential aptamer candidates.

An Illumina (San Diego, CA, US) MiniSee™ system was used to sequence the aptamer libraries after the post-parallel selection using a single-end read technique. Deep sequencing and subsequent data analysis simplifies the traditional approach of performing a large number of screening rounds (SchUtze et al., 2011). Numerous sequences were analyzed from the parallel-exposed final libraries. From these sets of data, the library sequence families were constructed at 90% homology (sequence similarity considering mutations, deletions, and insertions).

Bioinformatics and Aptamer Candidate Selection: An individual sequence's frequency in the positive target population was factored in, but the degree of variation between similar sequences was also important, with 90% homology being the minimum requirement (100% match over the entire sequence is not necessary to join a family; up to 2 bases can be mismatched, inserted, or deleted).

One factor is the presence of a sequence in the non-positive-target-exposed populations. Four libraries were collected for sequencing: the post-parallel assessment library that had been recovered from incubation with a positive target in 1× SELEX buffer; post-parallel assessment library recovered after incubation with counter targets in 1× SELEX buffer; post-parallel assessment library recovered after incubation with 1× SELEX buffer only; and the parallel assessment library recovered from incubation with PGN in 1× SELEX buffer. The positive population was compared against the counter population to identify sequences that were not removed during the counter selection steps, but which still had affinity for both the counter targets and PGN. A candidate's rate of enrichment was also considered (see, e.g., Wang et al., 2014). 200 candidates were chosen for microarray synthesis and high throughput assessment.

Figure 1:
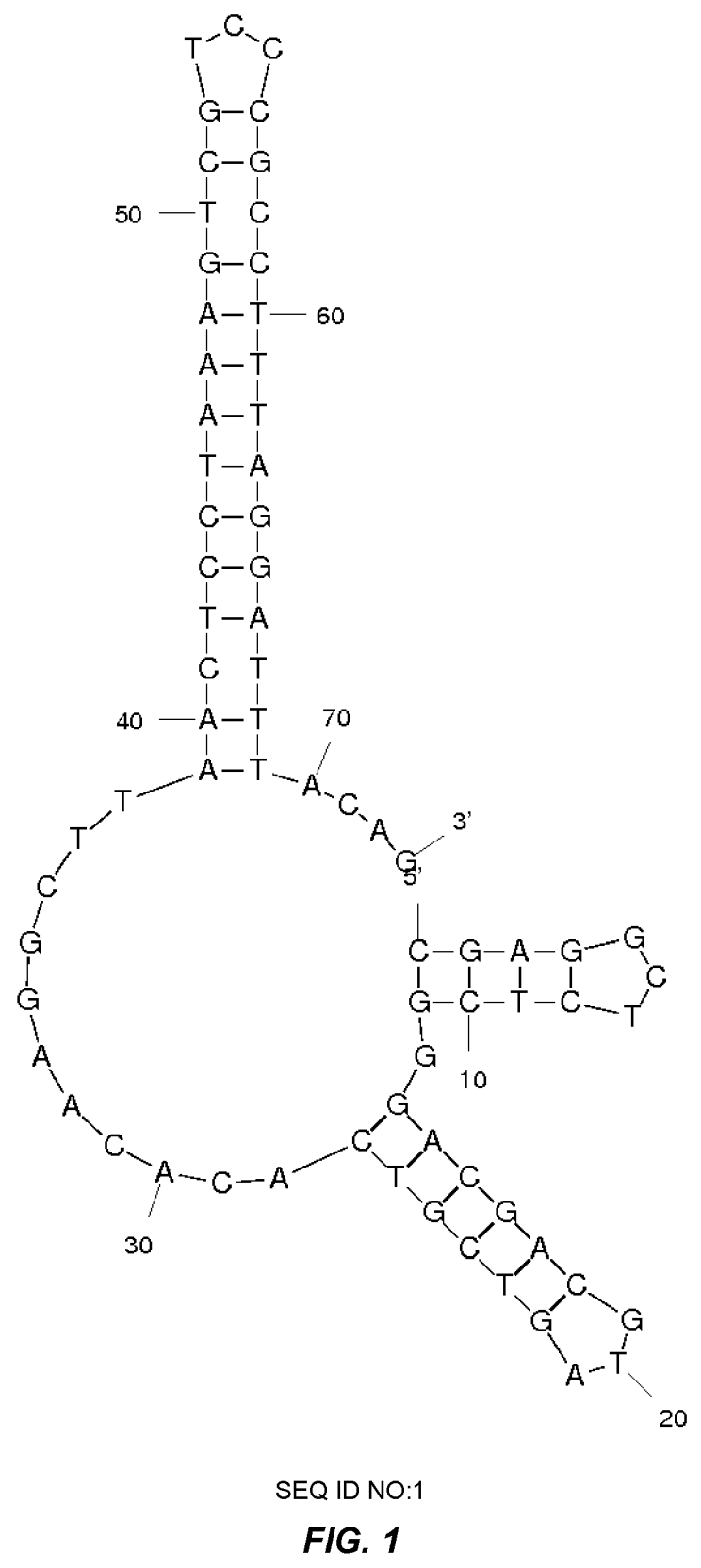
Figure 2:
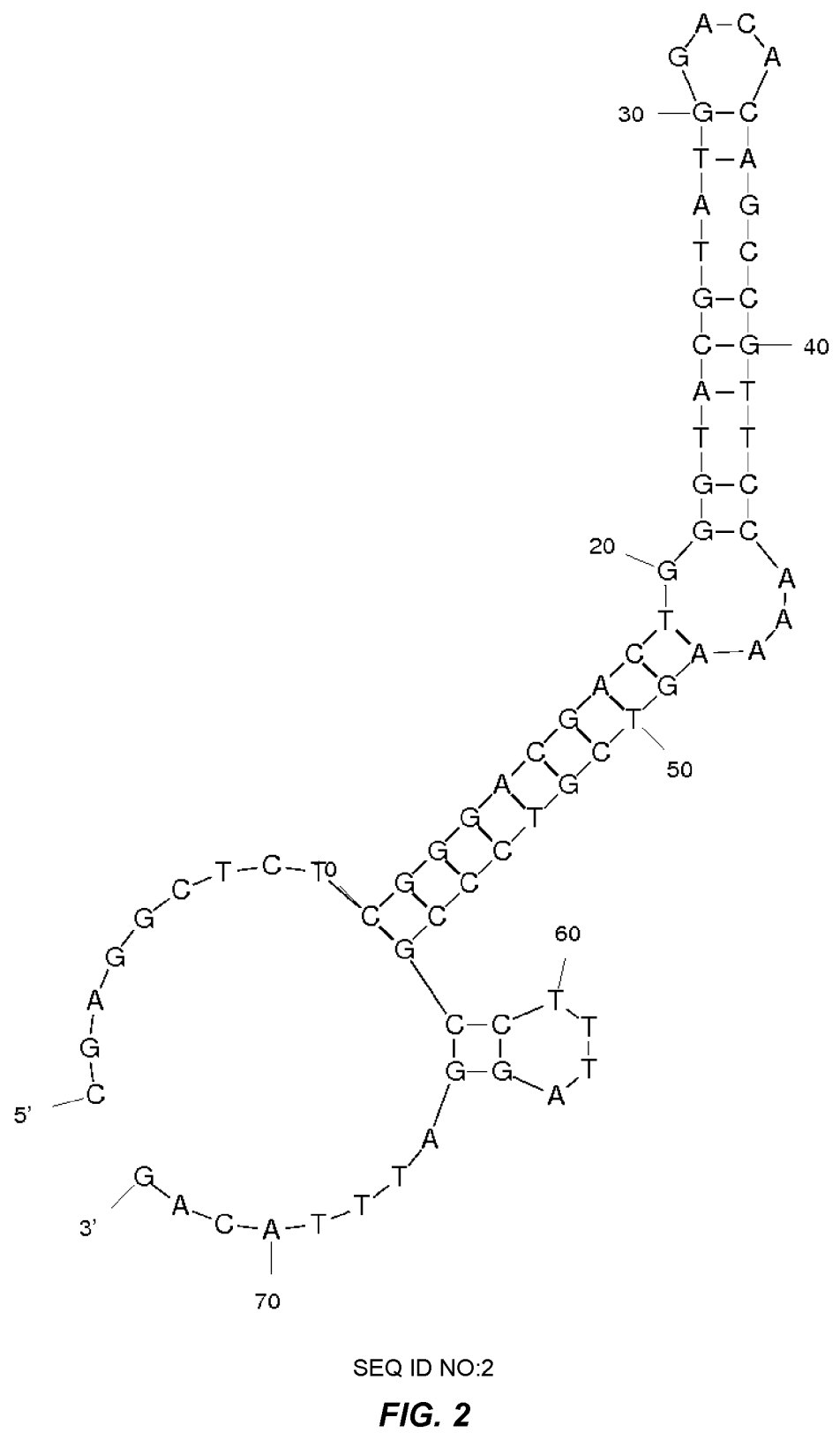
Figure 4:
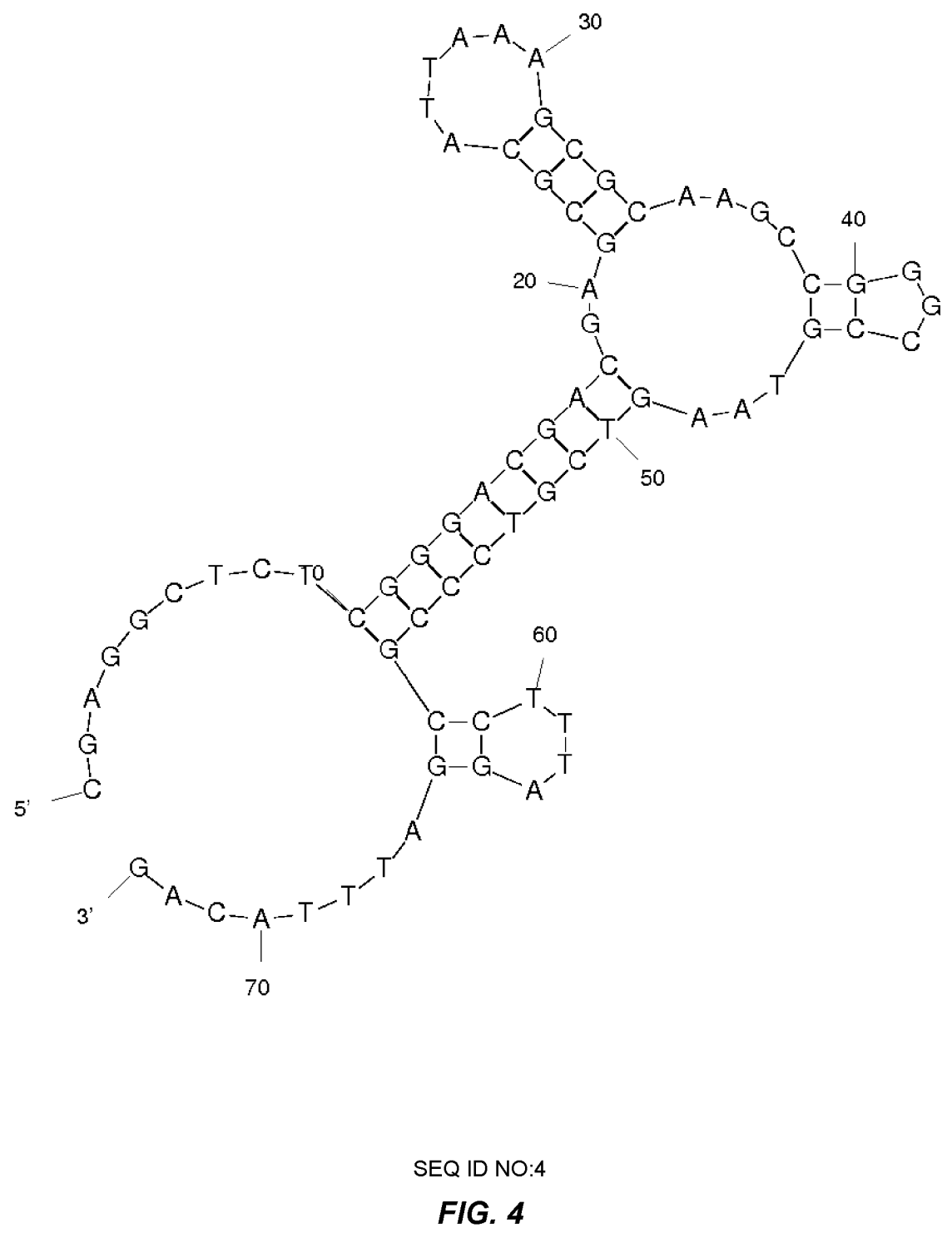
Figure 5:
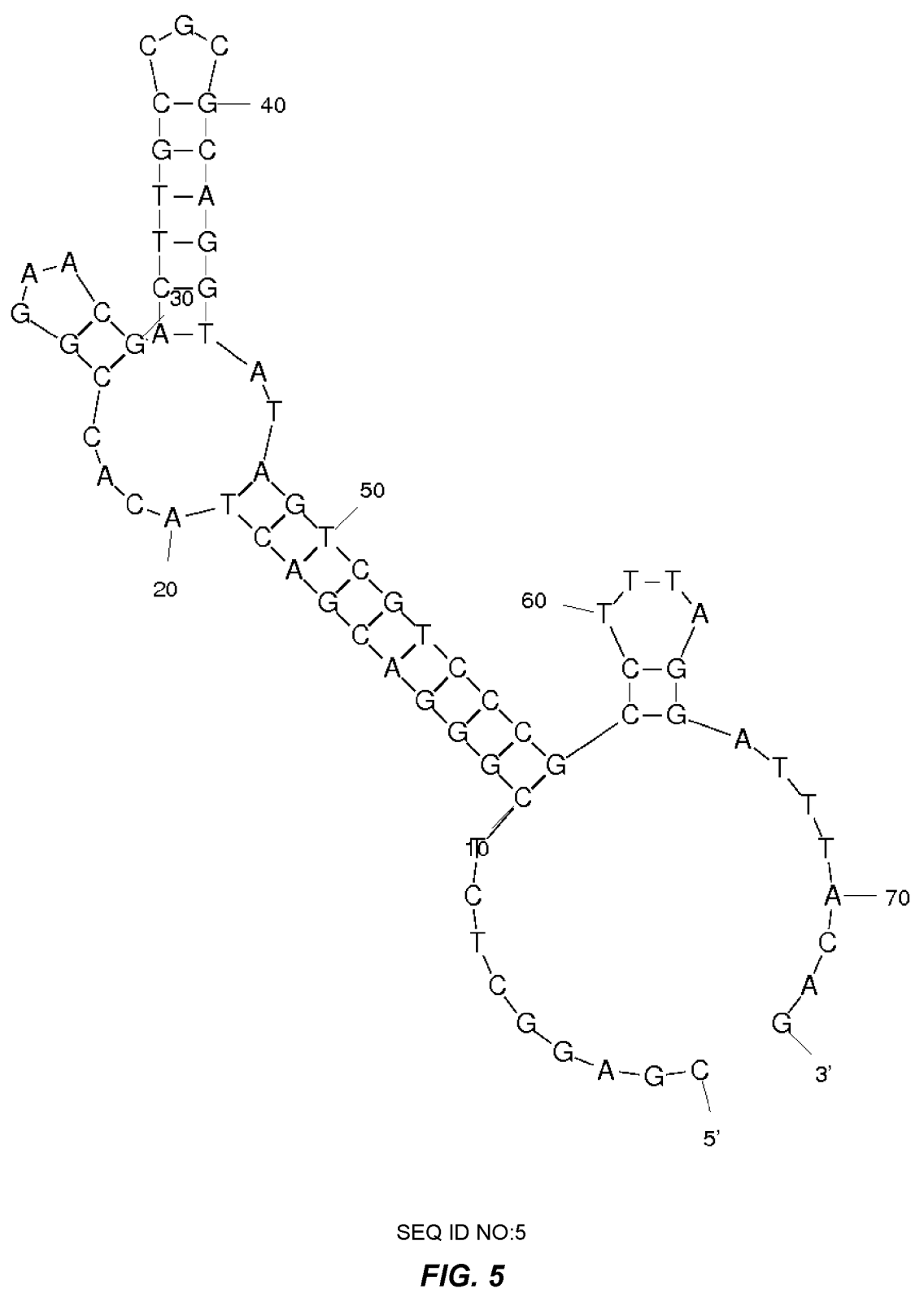

From these 200 aptamer candidates, SEQ ID NOs: 1-5 were specifically identified as examples of the selection process (FIGS. 1-5, respectively). The most prevalent family in the population is also highly present in the counter population. However, this sequence (and similar sequences) appeared at high enough frequencies in the positive populations to be still worth investigating in a high-throughput analysis. SEQ ID NOs: 1-5 were selected on the basis of greater proportional representation in the positive population over the counter population and/or negative population.

Finally, all candidate sequences exhibited sufficient stability based upon mfold secondary structure prediction to be considered candidates (FIGS. 1-5).

Microarray Synthesis and Semi-Quantitative Assessment

Microarray Methods: A Cy5-labeled reporter oligonucleotide complimentary to a constant region of the library (5'-GTC GTC CCG AGA GCC TCG/3Cy5Sp/-3' (SEQ ID NO:24)) was synthesized. SEQ ID NO:24 would be displaced during target binding. Oligonucleotides underwent desalting purification.

The mean background fluorescence value was subtracted from the mean fluorescence value of each candidate prior to the addition of sample as well as each candidate after the addition of sample.

Microarray Results: Candidates were first tested against 100 ng/mL target PGN sample. The result of blocking candidates with Reporter oligonucleotide was imaged. Based upon the image, most candidates interacted well with the Reporter. After this reading was taken, candidates were incubated with target sample overnight at 23° C. The solution at the inlet of the peristaltic pump was then replaced with 1× SELEX buffer to displace the target sample in the microarray.

The same processes were used to analyze candidate response to 1 μg/mL of counter target PGN sample, of which the second run data is presented.

Candidate percent responses to target sample and counter target sample were calculated as the mean of 18 replicate positions. The percent responses themselves were compared to determine candidates that specifically responded to the target. Candidates were ranked according to the ratio of signal loss to the target condition against the signal loss to the counter condition. The greater this score, the more response to the target condition relative to the response to the counter condition. The aptamer candidates with the top five scores (SEQ ID NOs.: 6-10) were then synthesized for qualitative assessment.

Monoclonal Synthesis and Qualitative Validation:

Assessment Methods: SEQ ID NOs.: 6-10 were synthesized and purified by desalting. Assessment followed a method similar to that used in the previously described SELEX.

Assessment Results: Initial assessment was carried out with SEQ ID NOs.: 6-10 against just target PGN in 1× SELEX Buffer to determine which candidates demonstrated noticeable response. Differences in the intensity of material present in the candidate lanes represented different amounts of candidate released from magnetic beads as a result of incubation with, and binding to, target PGN. Based upon these results, candidates SEQ ID NO:8 and SEQ ID NO:10 were selected for additional assessment.

Example II

An aptamer comprising a core sequence selected from the group consisting of SEQ ID NOs: 11-21 is appropriately labeled with quenching labels and used in an assay to detect PGN in a medical sample taken from a patient (e.g., peritoneal dialysis effluent). The assay is thus used to detect the presence of bacteria in the medical sample so as to diagnose an infection in the subject for treatment with an appropriate antibiotic.

REFERENCES (the contents of the entirety of each of which is incorporated herein by this reference):

Ellington and Szostak "In vitro selection of RNA molecules that bind specific ligands." Nature 1990, 346, 818.

Ferreira et al. "Selection of peptidoglycan-specific aptamers for bacterial cells identification." Appl Biochem Biotechnol. 2014 Dec; 174(7):2548-56. doi: 10.1007/s12010-014-1206-6. Epub 2014 Sep. 4. PMID: 25185503.

Gold et al. "Aptamers and the RNA world, past and present." Cold Spring Harb. Perspect. Biol. 2012, 4, a003582.

Schütze et al. "Probing the SELEX Process with Next-Generation Sequencing" PLoS ONE 6(12): e29604 (2011). DOI: 10.1371/journal.pone.0029604.

Tuerk et al. "Systematic evolution of ligands by exponential enrichment: RNA ligands to bacteriophage t4 DNA polymerase." Science 1990, 249, 505-510.

Wang et al. "Particle Display: A Quantitative Screening Method for Generating High-Affinity Aptamers" Angewandte Communications International Edition 53: 4796-4801 (2014). DOI: 10.1002/anie.201309334.

Zhang, W. "Synthesis of peptidoglycan peptides for DNA aptamer selection" (T). University of British Columbia (2018). Retrieved from open.library.ubc.ca/collections/ubctheses/24/items/1.0372791.

Zhuo et al. "Recent Advances in SELEX Technology and Aptamer Applications in Biomedicine" Int. J. Mol. Sci. 2017, 18, 2142; doi:10.3390/ijms18102142.

M. Zuker "Mfold web server for nucleic acid folding and hybridization prediction." Nucleic Acids Res. 31(13): 3406-3415 (2003). mfold.rna.albany.edu/?q=DINAMelt/Quickfold.

U.S. Patent Application Publication 20200249228 A1 to Jiang et al. (Aug. 6, 2020) for "Rapid Diagnosis of Peritonitis in Peritoneal Dialysis Patients".

What is claimed is:

1. A DNA aptamer comprising a polynucleotide comprising a core sequence set forth in any one of SEQ ID NOs: 11-20 and capable of binding to peptidoglycan ("PGN").

2. The DNA aptamer of claim 1, wherein the aptamer has a loop structure.

3. The DNA aptamer of claim 1, wherein the aptamer has a double-stranded stem structure.

4. The DNA aptamer of claim 1, further comprising at least one labeling substance.

5. The DNA aptamer of claim 4, wherein the labeling substance is an optical label, an electrochemical label, a radioisotope, or a combination thereof.

6. The DNA aptamer of claim 1, wherein the DNA aptamer has the core sequence of SEQ ID NO:11.

7. The DNA aptamer of claim 1, wherein the DNA aptamer has the core sequence of SEQ ID NO: 12.

8. The DNA aptamer of claim 1, wherein the DNA aptamer has the core sequence of SEQ ID NO: 13.

9. The DNA aptamer of claim 1, wherein the DNA aptamer has the core sequence of SEQ ID NO:14.

10. The DNA aptamer of claim 1, wherein the DNA aptamer has the core sequence of SEQ ID NO:15.

11. The DNA aptamer of claim 1, wherein the DNA aptamer has the core sequence of SEQ ID NO: 16.

12. The DNA aptamer of claim 1, wherein the DNA aptamer has the core sequence of SEQ ID NO:17.

13. The DNA aptamer of claim 1, wherein the DNA aptamer has the core sequence of SEQ ID NO:18.

14. The DNA aptamer of claim 1, wherein the DNA aptamer has the core sequence of SEQ ID NO:19.

15. The DNA aptamer of claim 1, wherein the DNA aptamer has the core sequence of SEQ ID NO:20.

16. The DNA aptamer of claim 1, further comprising: SEQ ID NO:22 and/or SEQ ID NO:23.

17. A method of detecting peptidoglycan ("PGN") in a sample, the method comprising:

utilizing the DNA aptamer of claim 1 to detect the PGN in the sample.

18. The DNA aptamer of claim 1, wherein the DNA aptamer is fixed to a substrate.

19. The DNA aptamer of claim 18, further comprising:

a linker between the substrate and the DNA aptamer.

20. The DNA aptamer of claim 1, together with aptamers to peptidoglycan (PGN) and aptamers to lipoteichoic acid (LTA) and/or lipopolysaccharide (LPS), all of said aptamers being configured in an assay for consecutive workflow.

21. A method of using the DNA aptamer of claim 1, the method comprising:

first detecting the presence of bacteria in a sample with the DNA aptamer, and then further characterizing detected bacteria afterword as Gram negative or Gram positive.

22. The method according to claim 21, wherein the sample is peritoneal dialysis effluent taken from a dialysis patient.

* * * * *